United States Patent
Berger et al.

(10) Patent No.: US 10,130,256 B2
(45) Date of Patent: Nov. 20, 2018

(54) MEDICAL DEVICE WITH OPTICAL TRANSFER OF DATA AND OPTICAL READING DEVICE FOR RECEIVING SUCH DATA

(71) Applicant: Sanofi-Aventis Deutschland GmbH, Frankfurt am Main (DE)

(72) Inventors: Lars Berger, Frankfurt am Main (DE); Marcus-Meinolf Dittrich, Frankfurt am Main (DE); Anton Petkov, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 83 days.

(21) Appl. No.: 14/651,237

(22) PCT Filed: Dec. 13, 2013

(86) PCT No.: PCT/EP2013/076568
§ 371 (c)(1),
(2) Date: Jun. 11, 2015

(87) PCT Pub. No.: WO2014/095644
PCT Pub. Date: Jun. 26, 2014

(65) Prior Publication Data
US 2015/0320314 A1 Nov. 12, 2015

(30) Foreign Application Priority Data
Dec. 18, 2012 (EP) .................................... 12197883

(51) Int. Cl.
*A61B 5/00* (2006.01)
*G06K 7/14* (2006.01)
*G06K 19/06* (2006.01)

(52) U.S. Cl.
CPC .......... *A61B 5/0004* (2013.01); *A61B 5/0017* (2013.01); *A61B 5/742* (2013.01); *G06K 7/1417* (2013.01); *G06K 19/06037* (2013.01)

(58) Field of Classification Search
CPC ........................ G06K 7/10732; G06F 19/328
(Continued)

(56) References Cited

U.S. PATENT DOCUMENTS

| 4,944,304 A | 7/1990 | Nishina |
| D542,681 S | 5/2007 | Young |

(Continued)

FOREIGN PATENT DOCUMENTS

| EP | 1826705 A1 | 8/2007 |
| EP | 2484283 A2 | 8/2012 |

(Continued)

OTHER PUBLICATIONS

English Translation of First Office Action issued in Chinese Patent Application No. 201380064552.2 dated Nov. 6, 2016.
(Continued)

*Primary Examiner* — Fabricio R Murillo Garcia
(74) *Attorney, Agent, or Firm* — McCarter & English, LLP (57) ABSTRACT

The invention relates to a medical device in combination with an optical reading device comprising at least one sensor, a meter display for displaying a matrix of pixels and a meter control unit adapted for controlling the meter display so that at least one measurement value measured by the sensor and/or a value derived thereof is encoded in an optical machine-readable signal, wherein the optical reading device is adapted to read the optical machine-readable signal from the medical device, to decode the optical machine-readable signal and to generate a message corresponding to the decoded optical machine-readable signal.

16 Claims, 5 Drawing Sheets

(58) Field of Classification Search
USPC .......................................... 235/462.42; 705/2
See application file for complete search history.

(56) References Cited

U.S. PATENT DOCUMENTS

| | | | |
|---|---|---|---|
| D611,489 S | 3/2010 | Bell et al. | |
| 8,131,478 B2 | 3/2012 | Kai | |
| 8,448,866 B2 | 5/2013 | Harttig et al. | |
| 2004/0077960 A1* | 4/2004 | Tanaka .................. | A61B 5/486 600/504 |
| 2004/0167414 A1* | 8/2004 | Tanabe ..................... | A61B 5/02 600/500 |
| 2007/0040449 A1 | 2/2007 | Spurlin et al. | |
| 2007/0145137 A1* | 6/2007 | Mrowiec ................. | A61B 5/00 235/462.01 |
| 2010/0056895 A1 | 3/2010 | Temple et al. | |
| 2010/0271213 A1* | 10/2010 | Krainz ............... | A61B 5/14532 340/573.1 |
| 2011/0071464 A1* | 3/2011 | Palerm ............... | A61B 5/14532 604/66 |
| 2011/0132778 A1 | 6/2011 | Austera et al. | |
| 2017/0181652 A1* | 6/2017 | Durand .............. | A61B 5/04001 |

FOREIGN PATENT DOCUMENTS

| | | |
|---|---|---|
| JP | S64-46432 A | 2/1989 |
| JP | 200924638 A | 2/2009 |
| WO | 2005104933 A1 | 11/2005 |
| WO | 2011117212 A1 | 9/2011 |

OTHER PUBLICATIONS

English Translation of Abstract of Japanese Patent Application No. 2009-027638 dated Nov. 3, 2017.

English Translation of Notice of Reason(s) for Rejection issued in Japanese Patent Application No. 2015-547052 dated Oct. 10, 2017.

* cited by examiner

MEDICAL DEVICE WITH OPTICAL TRANSFER OF DATA AND OPTICAL READING DEVICE FOR RECEIVING SUCH DATA

CROSS REFERENCE TO RELATED APPLICATIONS

The present application is a U.S. National Phase application pursuant to 35 U.S.C. § 371 of International Application No. PCT/EP2013/076568 filed Dec. 13, 2013, which claims priority to European Patent Application No. 12197883.7 filed Dec. 18, 2012. The entire disclosure contents of these applications are herewith incorporated by reference into the present application.

FIELD OF INVENTION

The invention relates to a medical device, for example a drug delivery device for injecting a drug or medicament, such as insulin, growth hormone and/or the like or a medical test meter in combination with an optical reader device.

BACKGROUND

Patient self-monitoring of physiological and/or medical parameters like blood glucose, heart rate or blood pressure is a vital component of the effective therapy of chronic diseases like diabetes, hypertension or renal failure. As an example, major clinical trials of insulin-treated patients that demonstrated the benefits of intensive glycemic control on diabetes complications have included patient self-monitoring of blood glucose as part of multifactorial interventions. Self-monitoring of blood glucose allows patients to evaluate their individual response to therapy and assess whether glycemic targets are being achieved. Results of self-monitoring of blood glucose can be useful in preventing undesired therapy outcomes such as e.g. hypoglycemia and/or in modifying behaviour to better achieve desired outcomes, such as e.g. adjusting medications (particularly prandial insulin doses)/diet/ and physical activity. Also, taking into account the amount of medication received from a delivery device such as an electronic drug delivery device can support a patient to reach therapeutic targets or improve the outcome of a therapy.

From the state of the art, medical test meters are known that provide information to the user by means of a graphical user interface. Electronic drug delivery devices comprising a graphical user interface are also known. Such devices are sometimes capable of storing data related to the use of the device, for instance, dose history information.

U.S. Pat. No. D542,681 S describes a design for a graphical user interface of an analyte test meter that provides information on the last measurement value taken, on a plurality of measurement values taken in the past and on an average value over a plurality of measurement values.

U.S. Pat. No. D611,489 S describes a design for a graphical user interface of an analyte test meter that provides information on a blood glucose status and textual instruction to the user.

Also medical test meters that communicate with an external device are known from the state of the art. EP 2 484 283 A2 relates to a blood glucose meter comprising a blood glucose measuring module for performing a blood glucose measuring function and a wireless communication module adapted for establishing a wireless communication link with an external device and exchanging information with the external device via the wireless communication link according to a predetermined frequency format and protocol. The blood glucose measuring module and the wireless communication module are physically separate units electrically connected in order to allow for an exchange of electrical signals corresponding to information to be transmitted by the wireless communication module and/or information received by the wireless communication module.

SUMMARY

It is an object of the present invention to provide an improved medical device, for example an drug delivery device for injecting a drug or medicament, such as insulin, growth hormone and/or the like or an improved medical test meter in combination with an optical reader device for reading data from such a medical device or test meter and for transforming it into an explanatory message, with at least one sensor, a meter control unit and a meter display controlled by the meter control unit.

The object is achieved by a medical device in combination with an optical reader device according to claim 1. The object is furthermore achieved by a method for generating an explanatory message according to claim 0.

Preferred embodiments of the invention are given in the dependent claims.

In accordance to the present invention, a medical device in combination with an optical reader device comprises at least one sensor, a meter display for displaying a plurality of independently controllable display elements and a meter control unit adapted for controlling the meter display so that at least one measurement value measured by the sensor and/or data derived thereof is encoded in an optical machine-readable signal, wherein the optical reading device is adapted to read the optical machine-readable signal, to decode the optical machine-readable signal and to generate a message corresponding to the decoded optical machine-readable signal.

An optical machine-readable signal is characterized by a variation of the brightness of at least one independently controllable display element in a predetermined geometrical arrangement. Information such as a measurement value can be encoded in a static manner by assigning each out of a plurality of independently controllable display elements a brightness value depending on its position. Information can also be encoded in a dynamic manner by a common variation of brightness of a plurality of independently controllable display elements over time. Information can further be encoded by independent variation of brightness of disjoint subsets of adjacent independently controllable display elements.

The independently controllable display elements can be formed as pixels that are arranged in a rectangular matrix.

Due to the predetermined geometrical arrangement of the independently controllable display elements it is possible to sample and decode the said variation of brightness by an optical reading device, wherein the geometrical arrangement of photosensitive elements is aligned with the geometrical arrangement of the independently controllable display elements. Thus, said variation of brightness forms an optical machine-readable signal.

The independently controllable display elements can be formed as switchable display elements so that they can be controlled as to be switched either on or off. The independently controllable display elements can also be controlled as to vary their brightness and/or colour in discrete steps.

According to a first aspect of the invention, the meter control unit controls the meter display so that a plurality of independently controllable display elements encode, by their brightness and according to a predetermined encoding scheme, at least one measurement value retrieved from a sensor and/or a value derived thereof as an optical machine-readable signal. Thus an optical reading device with a corresponding geometrical arrangement of photosensitive elements is able to decode the at least one measurement value retrieved from the sensor or the value derived thereof As an example, it is possible to encode one out of $2^n$ distinct measurement values by a plurality of n pixels of a meter display in a predetermined geometrical arrangement that can be controlled to be either dark or bright. As a further example, it is possible to encode one out of $b^n$ distinct measurement values by a plurality of n pixels of a meter display in a predetermined geometrical arrangement, wherein the brightness of a pixel can be controlled in b steps between dark and bright.

When formed as a medical test meter, it is a particular advantage of the invention that information related to measurements taken with the medical test meter forms the data that can be transferred to a physically separated optical reading device that displays, processes and/or stores said measurement-related information without the need of manually re-typing said measurement-related information and without the need of dedicated communication means such as a wireless adapter or an electrical connection. As an advantage, medical test meters known from the state of the art that usually comprise relatively small meter displays can be extended according to the present invention without hardware modification or an increased cost of goods.

The sensor may also comprise a clock so that both a measurement taken with the medical test meter and a time stamp assigned thereto form the data to be encoded by the meter display. It is also possible that such data is formed by time stamps related to certain interactions of the patient with the medical device, such as switching the device on or off or performing an injection, if the medical device is formed as a drug delivery device.

It is a further advantage of the invention that for a given number of independently controllable display elements of the meter display the encoding capacity is largely increased so that a larger number of distinct values can be encoded in an optical machine-readable signal than in a human-readable textual or graphical output of said meter display. In other words: either the processing of the output of a measurement value can be improved for a given number of independently controllable display elements, or the total number of independently controllable display elements can be reduced for a predetermined accuracy of the output.

It is possible that not all independently controllable display elements of the meter display are used for the encoding of a measurement value. For some applications it may be advantageous to use a first section of the meter display for displaying a user-readable textual and/or graphical message and to use a disjoint second section of the meter display for displaying an optical machine-readable signal. Furthermore, it is possible to design optical machine-readable signals that are readable by humans as well. For example, methods for optical character recognition (OCR) are known so that alphanumeric characters can be formed as machine-readable signals.

It is also possible to encode further information about the medical test meter such as the battery status, potential defects or warning codes aside the measurement values which increases the reliability and dependability of the test meter. Furthermore, it is possible to use error-detecting or error-correcting encoding schemes for the optical machine-readable signal so that an incorrect information transfer is prevented even in the presence of defect or disturbed independently controllable display elements.

In an embodiment the meter display comprises a plurality of independently controllable display elements of a predetermined geometrical form composed in a predetermined geometrical arrangement. As an example, an area of a liquid crystal display (LCD) that constitutes an independently controllable display element may be formed as an icon or as an predetermined alphanumeric character. In such an embodiment, the meter control unit and/or the meter display are adapted to form the optical machine-readable signal as a subset of independently controllable display elements that are switched on.

As an example, a meter display formed as an LCD may comprise a number n of independently controllable display elements. With such a meter display, $2^n$ distinct subsets of independently controllable display elements can be formed, where each subset differs from each other subset by at least one independently controllable element that is not in the same status, i.e. either switched on or switched off, in both subsets. Therefore, $2^n$ distinguishable optical machine-readable signals can be formed by such a meter display. Further, the brightness of pixel can be controlled in b steps between dark and bright by encoding one out of $b^n$ distinct measurement values by n pixels of the meter display.

As an advantage of this embodiment, meter displays from medical test meters known from the state of the art, which regularly comprise independently controllable display elements formed as icons and/or alphanumeric characters, can be extended to form optical machine-readable signals without additional hardware effort or cost of goods.

In an embodiment, the independently controllable display elements are formed as pixels of a substantially rectangular shape that are arranged in a matrix. In such an embodiment, the meter control unit and/or the meter display are adapted to form the optical machine-readable signal as a barcode. Various embodiments of such barcodes are known to those skilled in the art as for example Code 39, Code 93 or Code 128. As an advantage, such barcodes are easy to read and decode. As a further advantage, such barcodes are robust against a misalignment of the meter display and an optical reader.

In an embodiment, the independently controllable display elements are formed as pixels of a substantially rectangular shape that are arranged in a matrix and the meter control unit and/or the meter display are adapted to form the optical machine-readable signal as a two-dimensional code. Various embodiments of such two-dimensional barcodes are known to those skilled in the art as for example stacked two-dimensional barcodes like Code 49 or PDF 417 or matrix codes like quick response (QR) Code, DataMatrix, Maxi-Code or Aztec Code or, as a further example, dot codes like Snowflake Code or BeeTag. Such two-dimensional codes provide the advantage of a higher information density. As an example, more measurement values can be encoded in a two-dimensional code than in a barcode.

In an embodiment, the two-dimensional barcode is formed as a DataMatrix Code. As an advantage, the DataMatrix Code enables the correction of wrongly set pixels. Therefore, it is particularly robust against isolated defects in the pixel matrix of a meter display.

In an embodiment, the two-dimensional barcode is formed as a QR Code. QR-codes are known from the state of the art as robust, efficient and standardized encoding schemes for an optical machine-readable signal. Due to its standardization, algorithms and software applications for reading QR-codes are widely available. Therefore the identification of a measurement value that is encoded as a QR-code is significantly eased compared with the identification of a measurement value that is encoded as an optical machine-readable signal in a proprietary format.

It is a further advantage of this embodiment that QR-codes provide an error-correction algorithm such that an encoded measurement value can be correctly identified even if a significant number of pixels of the meter display fail. It is even possible to overlay textual information, e.g. a textual representation of a measurement value or some other information related to a measurement value, over a QR-code, without compromising the correct identification of the encoded information, so that a human-readable and a machine-readable optical signal can be advantageously combined.

In an embodiment, at least one independently controllable display element or pixel is varied in its brightness and/or colour over time, wherein the variation of the brightness and/or colour over time encodes the value of a measurement taken with the sensor and/or information related thereto. It is possible to control at least one particular independently controllable display element, in the following referred to as clock display element or pixel, such that its brightness and/or colour is varied according to a clock cycle provided by the meter control unit. By comparison with said clock cycle indicated by said clock display element or pixel, a plurality of two-dimensional codes forming an optical machine-readable signal can be encoded by the meter display. As an example, for each clock cycle, an independent two-dimensional code is issued by the meter display so that advantageously more information, like more measurement values, are transmitted by the meter display. As an even more specific example, one measurement value per clock cycle can be encoded as a two-dimensional code, so that the plurality of subsequent two-dimensional codes encodes a series of measurement values.

In an embodiment the meter control unit and/or the meter display are adapted to form the optical machine-readable signal as a variation over time of the brightness and/or colour of at least one segment of adjacent pixels.

The variation of the brightness and/or colour over time encodes the data provided by the medical device or test. As an example, all pixels of a meter display formed as a matrix of pixels can be controlled so as to simultaneously appear with the same brightness and/or colour. Various encoding schemes such as amplitude modulation, i.e. modulation of brightness, frequency modulation or pulse-width encoding are known to those skilled in the art. Due to the plurality of pixels that are controlled simultaneously, this embodiment is particularly robust with respect to single pixel failures and with respect to a misalignment between the meter display and an optical reading device. As a further advantage, such an embodiment requires a low total number of pixels and/or a low resolution of the meter display so that medical test meters known from the state of the art that usually comprise relatively small meter displays can be extended according to the present invention without hardware modification or an increased cost of goods.

For certain applications it can be advantageous to not control all independently controllable display elements of the meter display simultaneously, but to partition the meter display into disjoint meter display segments. Each meter display segment comprises one or a plurality of adjacent independently controllable display elements that are controlled simultaneously, but independent from the independently controllable display elements of other meter display segments. As an advantage, the information transfer capacity of such an arrangement of independent disjoint meter display segments can be multiplied.

To those skilled in the art, various geometrical arrangements of meter display segments are known. As an example, in an arrangement known as flicker code from the transfer of e-banking authorization codes, five meter display segments of a substantially rectangular shape formed by at least one independently controllable display element are arranged side by side, wherein the brightness of one of the meter display segments is varied periodically to transfer a clock. As algorithms and/or software applications for decoding flicker codes are widely available it is advantageous to adopt such a geometrical arrangement of meter display segments.

In an embodiment of the invention a sensor is formed as a sensor for measuring a blood analyte, in particular blood glucose.

According to the invention, blood glucose values measured with a medical test meter formed as a blood glucose meter can be transferred as an optical machine-readable signal from the blood glucose meter to a physically separated optical reading device where those blood glucose values are displayed, processed and/or stored.

The separated optical reading device can be chosen to have sufficient processing power, memory and a sufficient output periphery in order to transform the code value provided by the blood glucose meter into actionable explanatory messages. Those explanatory messages can provide feedback to the patient to guide his behaviour in order to improve his health status. As an example, the feedback can include positive reinforcement to encourage regular usage, helpful tips on how to test blood glucose or information on detected regularities or patterns like a variation of measured blood glucose values over time.

This embodiment is particularly useful for patient self-monitoring of blood glucose (SMBG). The processing power and the output periphery of the separated optical reading device enable informative, verbose explanatory messages that ease the proper interpretation of the measurement values. Those explanatory messages can guide the patient to adjust food intake, exercise, or pharmacological therapy to achieve specific glycemic goals. As the patient recognizes the value of such explanatory messages, his motivation to use the blood glucose meter regularly is strengthened.

In an embodiment the medical device according to the invention further comprises a meter storage unit for storing at least one measurement value and/or value derived thereof, wherein a plurality of measurement values and/or values derived thereof is encoded in the optical machine-readable signal.

As an advantage of this embodiment, a transfer of measurement values from the medical device to an optical reading device is required less frequently so that the operation of the medical device is eased.

As another advantage of this embodiment, further information such as the frequency of usage can be stored in the medical device and transferred as an optical machine-readable signal to the separated optical reading device. By this further information, more informative and precise explanatory messages can be generated that guide the patient.

As yet another advantage it is possible to apply detection algorithms on a plurality of measurement values on the medical test meter, as, for example, the recognition of trends or patterns in the measurement values. Those trends or patterns can be encoded as an optical machine-readable signal.

In an embodiment the medical device is formed as a drug delivery device and the sensor is adapted to measure at least one parameter of an injection. As an example, the medical device is formed as an electronic insulin injector for the therapy of diabetes, wherein the sensor is adapted to measure the point in time and the dosage of an insulin injection. Those parameters can be encoded as an optical machine-readable signal for a plurality of injections and transferred to the separated optical reading device where they form a journal of quantified therapeutic events. As an advantage, it is possible to track the compliance of a patient with a certain medication or to better identify adverse effects of a certain injection scheme over a longer period.

According to a second aspect of the invention, the optical reading device is adapted for reading data from a medical device or test meter according to the first aspect of the invention. The optical reader device comprises an optical receiver with at least one photosensitive element, a device storage unit, a device control unit and an device output unit, wherein an optical machine-readable signal received by the optical receiver is decoded by the device control unit and optionally stored by the device storage unit and wherein an explanatory message corresponding to the decoded optical signal is generated by the device control unit and issued by the device output unit.

The optical reading device is designed to operate as follows. For reading an optical machine-readable signal, the optical receiver can be brought into optical contact with the meter display so that the geometrical arrangement of the at least one photosensitive element is aligned with the geometrical arrangement of the independently controllable display elements or the at least one segment of the meter display. In other words: the photosensitive elements of the optical receiver are arranged such that the variation of the brightness of one independently controllable display element, for example one pixel, or one meter display segment of the meter display can be measured by at least one photosensitive element of the optical receiver.

The optical receiver decodes the optical machine-readable signal. As an example, the optical receiver detects corner markings of a square QR-code, determines the pixel brightness values inside the square and transforms the matrix of said pixel brightness values into the measurement value that was originally encoded in the medical test meter. As another example, the optical receiver demodulates an amplitude-modulated optical signal, e.g. a variation of the brightness of a meter display segment of pixels over time, and transforms the sequence of brightness values into the measurement value.

The optical receiver transfers the decoded information to the device control unit. From said information, the device control unit determines a storage location in the device storage unit where an explanatory message corresponding to the decoded information is stored. The device control unit retrieves this explanatory message from the device storage unit and transfers it to the device output unit.

It is possible that the device storage unit stores multiple explanatory messages corresponding to the decoded information. As an example, the device storage unit can store a plurality of translations of an explanatory message into different languages so that the device control unit can determine one out of a plurality of storage locations based on the current language setting of the optical reading device.

The device control unit transfers the explanatory message corresponding to the decoded information to the device output unit. As an example, the device output unit can be formed as an information display. Then the device output unit displays the explanatory message as textual and/or graphical output. The device output unit can also be formed as a loudspeaker. Then the explanatory message is issued as audible speech. The device output unit can furthermore be formed as an electronic communication unit such as a Universal Serial Bus (USB) adapter, a Bluetooth® adapter or a Global System for Mobile Communications (GSM) adapter. Then the explanatory message is sent electronically to a computer or a mobile phone. It is also possible to combine different embodiments of the device output unit in the optical reading device. As an example, the explanatory message can be displayed and simultaneously sent as an email or Short Message Service (SMS) message. Thus the patient is informed immediately on his current measurement value and can easily store and review previous explanatory messages using his personal digital assistant (PDA). Or, a caregiver or medical personnel is informed on the medical status of the patient via such data transfer as an email or SMS, thus further expanding the usefulness of the messages in cases where the message as such may require the involvement of such persons, e.g. when it is received by a minor.

It is an advantage of this embodiment that the device output unit and the device control unit of the optical reading device are not restricted e.g. by the geometrical footprint and the admissible power consumption of the medical test meter. Therefore, an explanatory message issued by the optical reading device enables a more detailed and verbose information of the patient with regard to the measurement taken with the medical test meter. As an example, an explanatory message can provide help to interpret a potential reason for a measurement value or a pattern comprising such values.

As a further advantage, the localisation of explanatory messages can be moved off the medical test meter and can be performed on the optical reading device instead. This eases the development, operational and sales process as well as the regulatory process for the medical test meter. As an example, the medical test meter can be handled as an internationally and/or regionally unique stock keeping unit (SKU).

In an embodiment according to the second aspect of the invention the optical receiver comprises a camera. From the state of the art, cameras are known that provide a sufficient spatial resolution and a sufficient time resolution to record an optical machine-readable signal for various encoding techniques. As an example, a camera can take images from a meter display that shows an optical machine-readable signal formed as a QR-code. A camera can also take a video stream or a sequence of images that records an optical machine-readable signal formed as a flicker code. Therefore, a camera is a versatile and cost-efficient component of an optical receiver.

In an embodiment according to the second aspect of the invention the device output unit is formed as an information display. It is a particular advantage of this embodiment that messages received and decoded by the optical receiver can be displayed as textual and/or graphical output. Such a textual and/or graphical output enables detailed, verbose and discreet information of the patient.

In an embodiment according to the second aspect of the invention the device control unit generates an explanatory message by processing a received and optionally a stored decoded optical machine-readable signal. According to this embodiment it is possible to provide the patient more than a few predetermined explanatory messages.

As an example, the device control unit can be formed as a microcontroller that runs a control program. The control program can evaluate the received and decoded optical machine-readable signal. Optionally, the control program can additionally retrieve from the device storage unit stored optical machine-readable signals that were received and stored previously. Thus, the control program can evaluate a more comprehensive context with regard to the current measurement value and generate more informative explanatory messages as it is the case with medical test meters known from the state of the art.

In an embodiment according to the second aspect of the invention the explanatory message comprises a recommendation on the behaviour of the user of the medical test meter so as to fulfil at least one predetermined criterion with regard to a value measured by the medical test meter. As an example, an undesirable trend or pattern of measurement values can be interpreted by the control program running on the device control unit so that a change of the medication or of a behavioural pattern of the patient is detected as a potential reason for said trend or pattern. Then the explanatory message can comprise tips or hints that may help to revert said undesirable trend or pattern and to improve the health status of the patient. Thus the patient can be taught regularly on how to use the measurement values provided by the medical test meter to adjust his behaviour like food intake or exercise and/or to adjust his pharmacological therapy.

In an embodiment according to the second aspect of the invention the device control unit comprises an inference engine for generating the explanatory message. Inference engines are known to those skilled in the art as state machines that process input data based on a set of predetermined inference rules and that select and/or adapt conclusions based on the input data and the set of rules. Inference engines may be formed as neural networks. Inference engines may also be formed as programs that implement statistical decision methods. It is possible to adapt inference engines based on the input data such that the conclusions derived by the inference engine are optimised with regard to a predetermined optimisation criterion.

It is an advantage of this embodiment that a generated explanatory message is adapted more precisely to the individual status of the patient so that the compliance of the patient with a recommendation is more likely and more likely successful.

In an embodiment according to the second aspect of the invention the optical reading device is formed as a mobile phone or personal digital assistant (PDA) comprising a camera, a processing unit, a storage unit and an information display and/or a speaker.

Such mobile phones and PDAs are widely available and in use. They can be adapted by a software program running on the processing unit so that images or videos of optical machine-readable signals can be taken with the camera and further on decoded by the processing unit. Then, the processing unit, the storage unit and the display of the mobile phone or PDA correspond to the device control unit, the device storage unit and the device display of an optical reading device, respectively. The display and the loudspeaker of the mobile phone or PDA correspond to embodiments of the device output unit of an optical reading device. Thus a mobile phone or a PDA adapted by such a software program forms an optical reading device.

The software program running on the processing unit can be adapted such that an explanatory message corresponding to the decoded optical machine-readable signals can be retrieved and/or adapted from messages stored on the storage unit and further on displayed as a textual and/or graphical output on the display. The explanatory message can also be issued as audible speech via the loudspeaker. The explanatory message can furthermore be sent electronically to a computer or another mobile phone.

It is a particular advantage of this embodiment that it makes use of a commonly used device familiar to the general public such as a mobile phone or a PDA for the generation and output of explanatory messages. For a patient that already owns a mobile phone or PDA, insignificant or no additional costs are associated with this embodiment. As a further advantage, it enables the patient to store and manage his measurement values in a familiar software environment.

According to a third aspect of the invention, a method for generating an explanatory message issued by an optical reading device according to the second aspect of the invention comprises the steps of:

retrieving an explanatory message by a search over a set of predetermined textual template messages, wherein an input signal is used as a search key and wherein the search is performed according to predetermined search rules adapting the explanatory message so that it comprises a recommendation on the behaviour of the user of the medical test meter so as to fulfil at least one predetermined criterion with regard to the input signal optionally translating the explanatory message according to a configurable localization setting, wherein the input signal comprises at least one decoded optical signal.

Advantageously an explanatory message generated according to this embodiment provides more detailed information on a measurement value or a plurality of measurement values than could be generated and/or displayed with a medical test meter known from the state of the art due to the limited processing and displaying resources of such a medical test meter. As a further advantage, an explanatory message generated according to this embodiment can be adapted more precisely to the individual status of the patient so that the compliance of the patient with a recommendation provided by said message is more likely and more successful.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
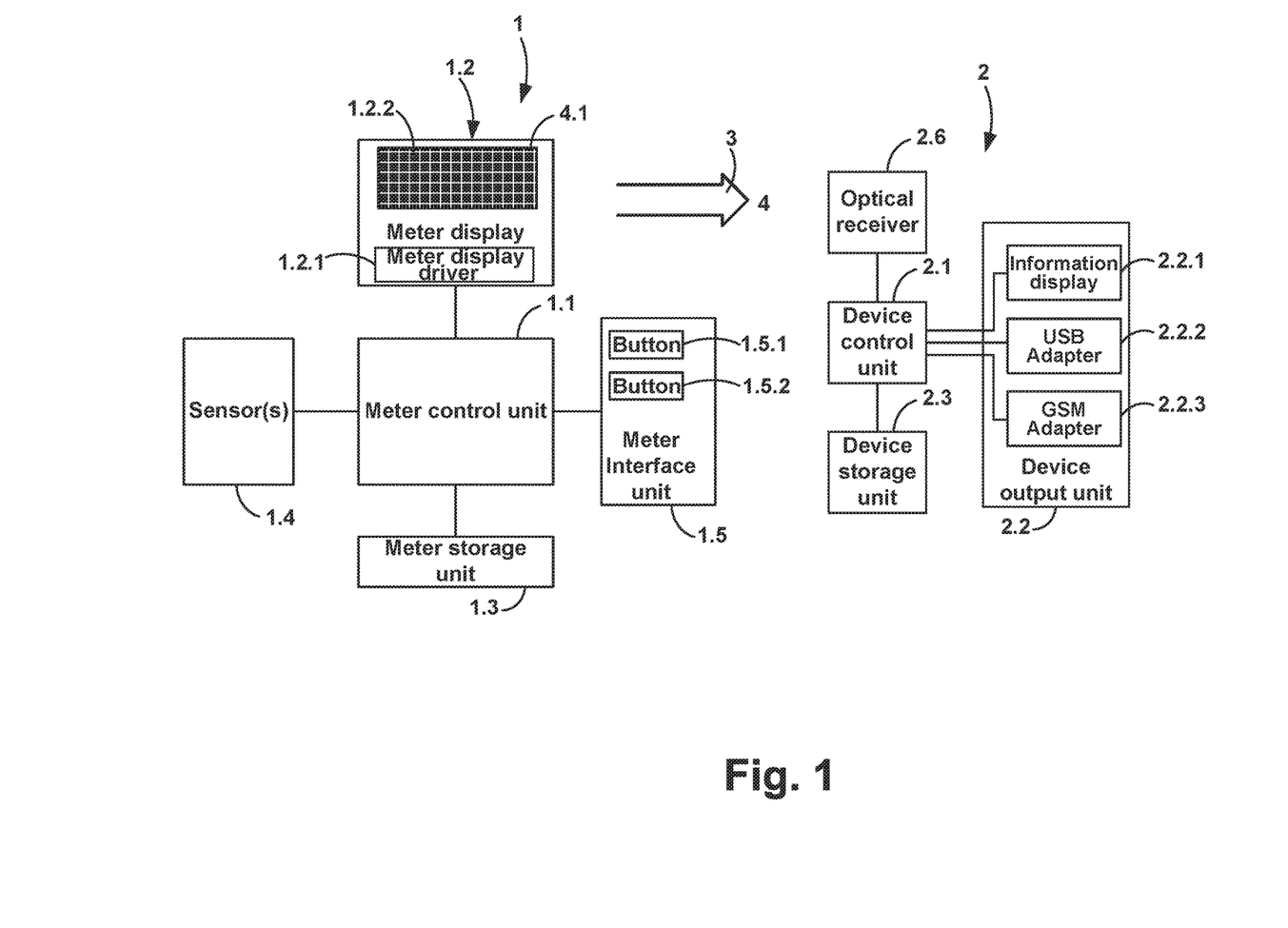
FIG. 1 schematically shows an optical reading device that is optically connected with a medical device, in particular a medical test meter, FIG. 2, FIG. 3, FIG. 4 and FIG. 5 schematically show embodiments of an optical machine-readable signal, FIG. 6 schematically shows an embodiment of a medical device with a mounted optical reading device, FIG. 7 schematically shows an embodiment of an optical reading device

FIG. 1 schematically shows a medical test meter 1 and an optical reading device 2 that are optically connected via an optical path 3.

The medical test meter 1 comprises a meter control unit 1.1 that is connected with a meter display 1.2, a meter storage unit 1.3, at least one sensor 1.4 and a meter interface unit 1.5.

The at least one sensor 1.4 comprises a means for measuring a physiological and/or medical parameter such as e.g. a means that is able to analyze blood samples on enzyme-based test strips, that can be inserted into a test strip receiving slot of the medical test meter 1 in order to determine the blood glucose level based on the enzymatic reaction or e.g. a means that is able to non-invasively measure the systolic and the diastolic arterial blood pressure. It is possible that the medical test meter 1 comprises a plurality of sensors 1.4 so as to measure different physiological and/or medical parameters.

The meter control unit 1.1 is connected with the at least one sensor 1.4 so as to receive measurement values taken with the sensor 1.4. The meter control unit 1.1 is furthermore connected with the meter display 1.2 so as to control the output of the meter display 1.2. It is possible that the meter display 1.2 comprises a meter display driver 1.2.1 that is able to receive high-level commands from the meter control unit 1.1 and that transforms these high-level commands into electrical signals controlling the appearance of the pixels 1.2.2 of the meter display 1.2.

The meter display 1.2 comprises a plurality of pixels 1.2.2 that are arranged in a regular grid or matrix and that can be controlled independent from each other. As an example, a meter display 1.2 can be formed as a liquid crystal display (LCD) comprising a plurality of substantially rectangular pixels 1.2.2 arranged as a matrix. A pixel 1.2.2 can be controlled so that it appears bright or dark. It is also possible that the brightness of a pixel 1.2.2 can be controlled gradually, e.g. continuously or in discrete steps. The display may also comprise independently controllable display elements to form characters and/or symbols or icons instead or in addition to the pixels. Such display elements may, for instance, be formed of seven bars arranged as a seven-segment-digit for displaying alphanumeric characters.

The meter control unit 1.1 is connected with a meter interface unit 1.5. The patient can initiate a measurement or the generation and display of an optical machine-readable signal 4 via the meter interface unit 1.5. The meter control unit 1.1 can be connected with a meter storage unit 1.3 to store and retrieve measurement values.

The optical reading device 2 comprises a device control unit 2.1 that is connected with a device output unit 2.2, a device storage unit 2.3 and an optical receiver 2.6. The device output unit comprises an information display 2.2.1, a USB adapter 2.2.2 and a GSM adapter 2.2.3. The device control unit 2.1 can be formed as a microcontroller that runs a device control program.

The device storage unit 2.3 stores a plurality of explanatory messages that can be retrieved by the device control unit 2.1 and transferred to the device output unit 2.2.

The optical receiver 2.6 receives and decodes an optical machine-readable signal 4. As an example, the optical receiver 2.6 can be formed as a camera that detects corner markings of a square QR-code displayed by the meter display 1.2, determines brightness values of pixels 1.2.2 inside the square and transforms the matrix of said pixel brightness values into the measurement value that was originally encoded in the medical test meter. As another example, the optical receiver 2.6 can demodulate an amplitude-modulated optical signal, e.g. a variation of the brightness of a plurality of pixels 1.2.2 over time, and transforms the sequence of brightness values into the measurement value.

The medical test meter 1 and the optical reading device 2 can be optically connected via an optical path 3. The optical path 3 can be formed by a focusing optics, e.g. one or more objective lenses, that is part of an optical receiver 2.6 formed as a camera. Then, the medical test meter 1 is brought into the focussing plane of the camera. The optical path 3 can also be formed as a direct illumination of photosensitive elements in the optical receiver 2.6, such as photodiodes. Then, the medical test meter 1 is brought into direct contact with the optical receiver 2.6 whereby the photosensitive elements face the meter display 1.2.

The medical test meter 1 and the optical reading device 2 are designed to operate as follows.

The patient initiates a measurement by the meter user interface 1.5. As an example, the medical test meter 1 is powered on via a first button 1.5.1, a test strip is inserted into the sensor 1.4 and a certain amount of blood or bodily fluid is applied on the test strip. Alternatively, a test strip is inserted into the sensor 1.4 and powers the medical test meter 1 on. Subsequently, a certain amount of blood or bodily fluid is applied on the test strip.

Applying of the blood sample on the test strip triggers an analytic algorithm implemented in the sensor 1.4 and/or the meter control unit 1.1 and a countdown is displayed on the meter display 1.2 accordingly.

The result of the analytic algorithm, a measurement value, for example a blood glucose value, is transferred via the meter display driver 1.2.1 to the meter display 1.2. The meter display 1.2 can show the measurement value as a short textual or iconic representation.

It is also possible that the optical reading device 2 is connected with a personal computer (PC) via a device output unit 2.2, for example formed as an USB adapter 2.2.2. Then, the monitor of the PC can be used as information display 2.2.1 for the presentation of data retrieved from the medical device 1. It is also possible to use both a built-in information display 2.2.1 and the monitor of the PC for the presentation.

Then, the patient may decide to transfer the acquired measurement value and, optionally, further measurement values acquired by previous measurements, to the optical reading device 2. For this purpose, the patient initiates the generation of an optical machine-readable signal 4 via the first button 1.5.1 or optionally via a second button 1.5.2. Such an explicit initiation advantageously avoids a confusion of an optical machine-readable signal with a defect or a corruption on a textual or graphical output.

It is also possible that the medical device or test meter 1 performs calculations or evaluations on at least one measurement value to generate supplemental information to be conveyed to the user by means of a display message. As an advantage, such a message can be presented by the information display 2.2.1 if it is too long to be shown on the meter display 1.2.

Then the meter control unit 1.1 issues a control command to the meter display driver 1.2.1. The meter display driver 1.2.1 controls the meter display 1.2 so that an optical machine-readable signal 4 is displayed at the meter display 1.2 or a part thereof. A plurality of adjacent pixels 1.2.2 may be controlled simultaneously and independent from other pixels 1.2.2, thus forming a meter display segment 4.1 on the meter display 1.2.

For reading an optical machine-readable signal 4, the optical receiver 2.6 is brought into an optical path 3 with the meter display 1.2 so that the geometrical arrangement of the at least one photosensitive element of the optical receiver 2.6 is aligned with the geometrical arrangement of the pixels 1.2.2 or the at least one meter display segment 4.1 on the meter display 1.2. In other words: the photosensitive elements of the optical receiver 2.6 are arranged such that the variation of the brightness of one pixel 1.2.2 or one meter display segment 4.1 on the meter display can be measured by at least one photosensitive element of the optical receiver 2.6.

The optical receiver 2.6 decodes the optical machine-readable signal 4 and transfers the decoded information to the device control unit 2.1. From said information, the device control unit 2.1 determines a storage location in the device storage unit 2.3 where an explanatory message corresponding to the decoded information is stored. The device control unit 2.1 retrieves this explanatory message from the device storage unit 2.3 and transfers it to the device output unit 2.2.

It is also possible that at least one device output unit 2.2 is adapted for a bidirectional communication, such as a GSM adapter 2.2.3 or a UMTS adapter. Then, it is possible that the device control unit 2.1 retrieves said explanatory message via a protocol supported by the at least one device output unit 2.2 adapted for a bidirectional communication. As an example, the optical reading device 2 may be formed as a smartphone, wherein a device control unit 2.1 formed as the smartphone's processor retrieves an explanatory message via an UMTS-based internet connection from a remote server. As an advantage of this embodiment, the content of an explanatory message can be updated, adapted, expanded or blocked by the remote server, for example in order to avoid adverse events that would otherwise result from using the optical reading device.

It is possible that the device control unit 2.1 retrieves multiple explanatory messages corresponding to the decoded information from the device storage unit 2.3 or via a device output unit 2.2 adapted for a bidirectional communication. As an example, the device storage unit 2.3 can store a plurality of translations of an explanatory message into different languages so that the device control unit 2.1 can determine one out of a plurality of storage locations based on the current language setting of the optical reading device 2.

The device control unit 1 transfers the explanatory message corresponding to the decoded information to the device output unit 2.2. As an example, the device output unit can be formed as an information display 2.2.1. Then the device output unit 2.2 displays the explanatory message as textual and/or graphical output. The device output 2.2 unit can also be formed as a loudspeaker. Then the explanatory message is issued as audible speech. The device output unit 2.2 can furthermore be formed as an electronic communication unit such as a Universal Serial Bus (USB) adapter 2.2.2, a Bluetooth® adapter or a Global System for Mobile Communications (GSM) adapter 2.2.3. Then the explanatory message is sent electronically to a computer or a mobile phone. It is also possible to combine different embodiments of the device output unit 2.2 in the optical reading device 2. As an example, the explanatory message can be displayed on the information display 2.2.1 and simultaneously sent as a Short Message Service (SMS) message via a GSM adapter 2.2.3. Thus the patient is informed immediately on his current measurement value and can easily review previous explanatory messages using his personal digital assistant (PDA). It is also possible to inform a caregiver or medical personnel on the health status of a patient this way.

Figure 2:
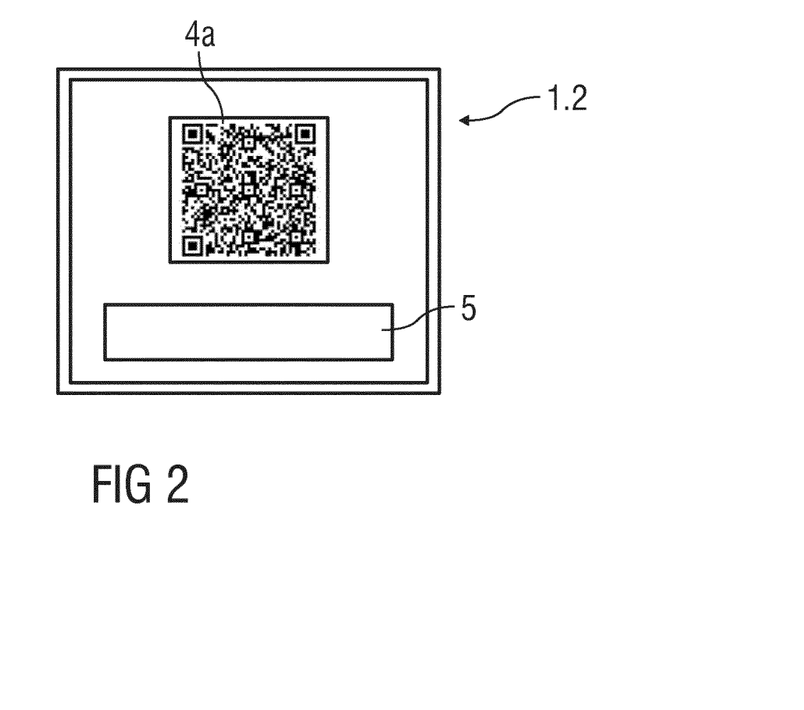

FIG. 2, FIG. 3, FIG. 4 and FIG. 5 schematically show optical machine-readable signals 4a, 4b, 4c, 4d displayed by the meter display 1.2. FIG. 2 shows a partitioning of the pixels 1.2.2 of the meter display 1.2 into an optical machine-readable signal 4a and a meter message region 5. The optical machine-readable signal 4a is formed as a static, i.e. time-invariant, image comprising a plurality of pixels 1.2.2 showing a QR code. This image can be transformed into a matrix of bit-values, wherein a dark pixel translates into a bit value of zero and a bright pixel into a bit value of one, respectively. The meter message region 5 shows short textual and/or iconic information on the acquired measurement value.

Figure 3:
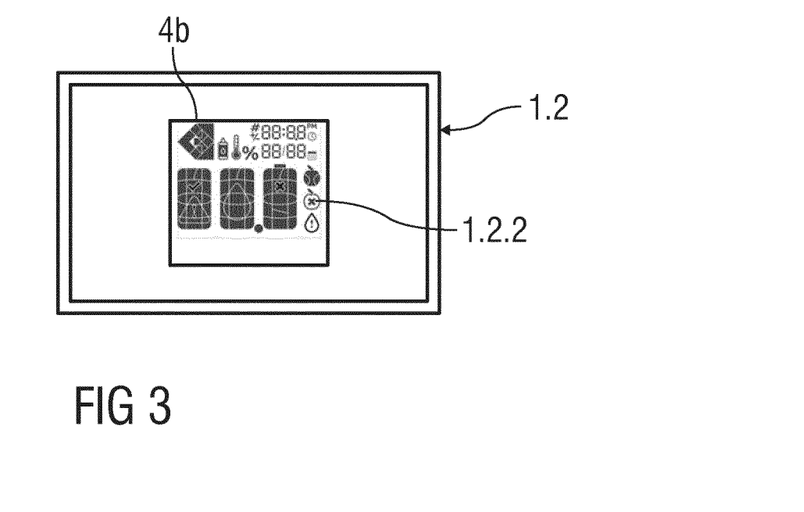
Figure 4:
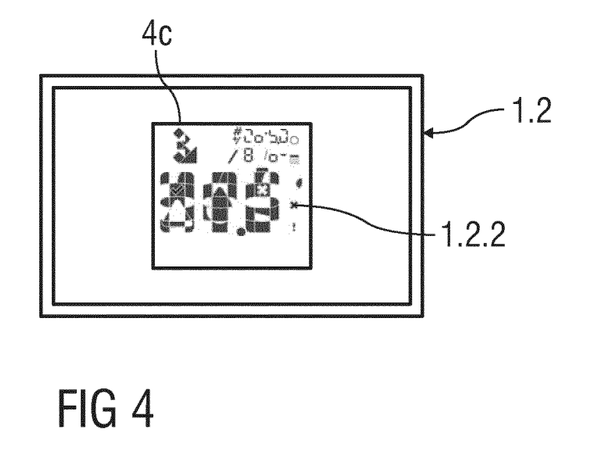

FIG. 3 schematically shows a meter display 1.2 that comprises a number n of independently controllable display elements 1.2.2 that form icons and seven-segment alphanumeric characters. As shown in FIG. 4, these independently controllable display elements 1.2.2 can be switched on and off independent from each other. As an example, single bars of a seven-segment digit are switched on while other bars of the same seven-segment digit are switched off. Also, some icons or parts thereof are switched on while other icons or parts thereof are switched off. Thus, FIG. 4 shows one out of $2^n$ distinct configurations to control the plurality of all display elements 1.2.2 of the meter display 1.2. Either all these $2^n$ distinct configurations or a subset thereof may form an optical machine-readable signal 4, 4a, 4b, 4c, 4d.

Figure 5:
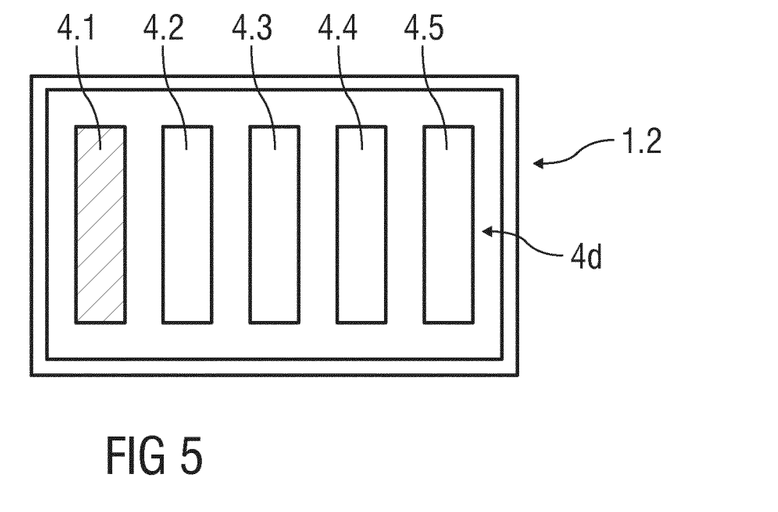

FIG. 5 shows an optical machine-readable signal 4d formed as a flicker code. The optical machine-readable signal 4d comprises five rectangular meter display segments 4.1, 4.2, 4.3, 4.4, 4.5 of adjacent pixels 1.2.2. The pixels 1.2.2 of a meter display segment 4.1, 4.2, 4.3, 4.4, 4.5 are controlled as to have the same brightness. The brightness of each of the meter display segments 4.1, 4.2, 4.3, 4.4, 4.5 is controlled independently. Thus each of the meter display segments 4.2, 4.3, 4.4, 4.5 can encode one out of four bits, where a low brightness encodes a bit value of zero, and a high brightness encodes a bit value of one, respectively. The brightness of the meter display segment 4.1 is changed periodically such to serve as a clock. By modifying the brightness of the meter display segments 4.2, 4.3, 4.4, 4.5 synchronous to said clock, a four-bit wide bit-stream can be encoded by the optical machine-readable signal 4d.

The meter display driver 1.2.1 generates the optical machine-readable signal 4a, 4b, 4c, 4d out of a bit pattern that constitutes, for example, the image of the QR-code of the optical machine-readable signal 4a or the bit-stream of the flicker code of the optical machine-readable signal 4d. The optical receiver 2.6 transforms the optical machine-readable signal 4a, 4b, 4c, 4d back into the original bit pattern. The bit pattern itself may encode one or more measurement values and/or information related to the measurement or to the medical test meter 1.

Figure 6:
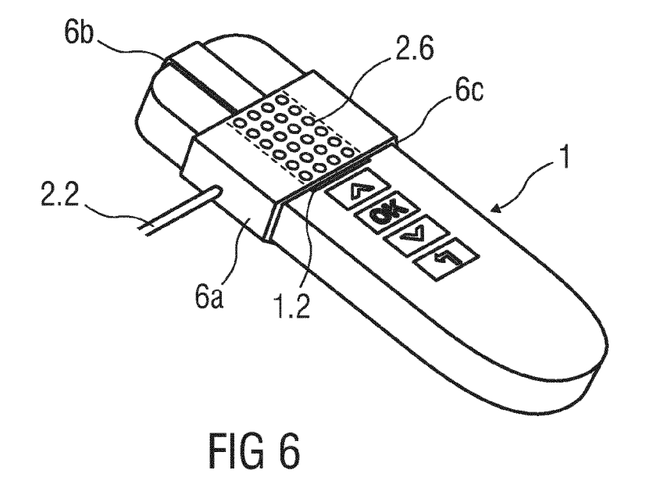

FIG. 6 shows a medical device 1 formed as an electronic drug delivery device. Beside buttons to prepare and operate the injection, the medical device 1 comprises a meter display 1.2 that, as an example, indicates the dosage and/or medication and/or time of injection. An optical reading device 2 is mounted on top of the meter display 1.2 so that an optical path is established between the optical receiver 2.6 of the optical reading device 2 and the meter display 1.2 of the medical device 1. Thus an optical machine-readable signal 4 issued by the meter display 1.2 is received by the optical receiver 2.6. In order to improve the stability of said optical path, the optical reading device 2 comprises mounting clips 6a, 6b, 6c for a substantially stiff but releasable mounting of the optical reading device 2 on the medical device 1.

Figure 7:
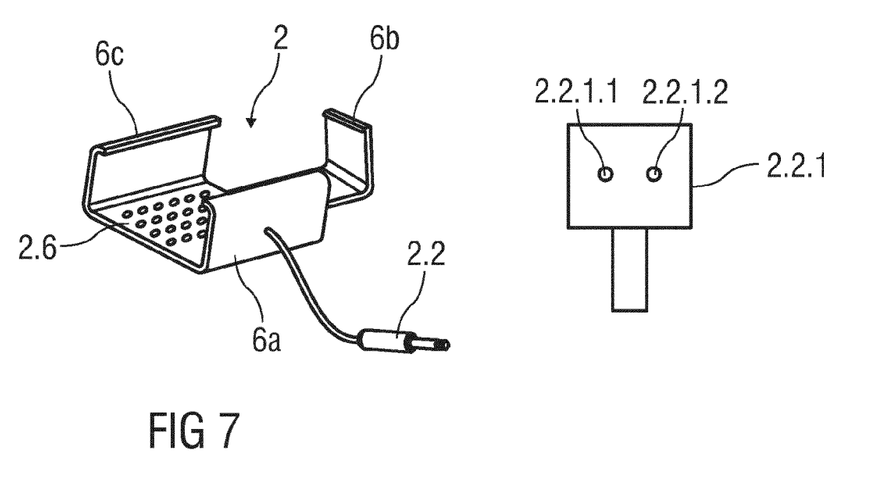

As shown in more detail in FIG. 7, the optical reading device 2 may comprise a simple information display 2.2.1 formed as one or a plurality of light emitting diodes (LEDs). As an example, a green LED 2.2.1.1 may indicate a successful injection process while a red LED 2.2.1.2 may indicate an error condition like an incomplete injection or a wrong dosage. Via a device output unit 2.2, that for example may be formed as an USB adapter 2.2.2, data issued by the meter display 2.1 and received by the optical receiver 2.6 can be transferred further to a personal computer or a personal digital assistant for a more versatile and precise presentation. As a particular advantage of the embodiment shown in FIG. 7 the meter display 1.2 is hidden by the information display 2.2.1, so that a potential confusion of the patient by an incomplete appearance of digits or symbols on the meter display 1.2 is avoided.

Figure 8:
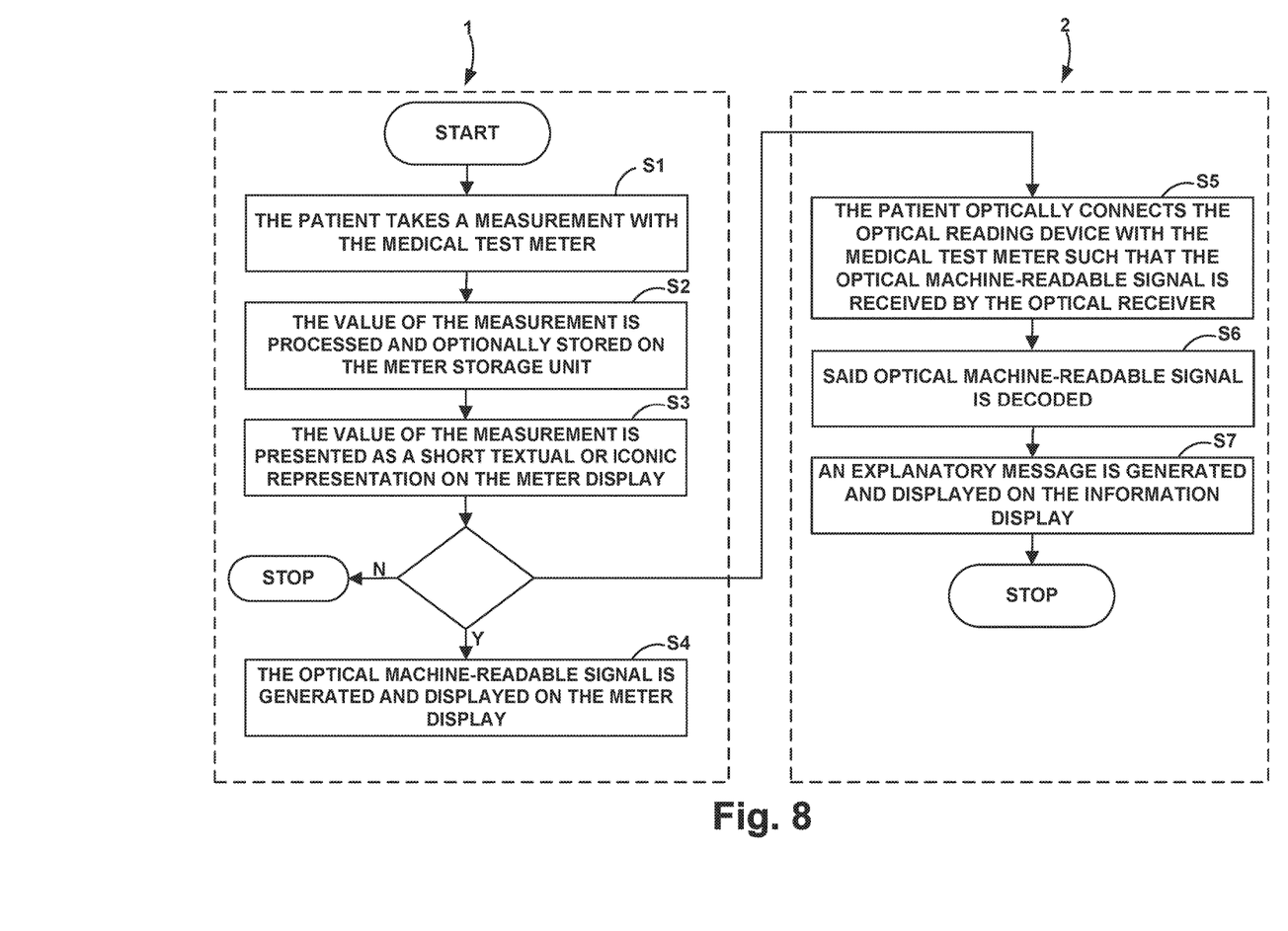
FIG. 8 shows the control flow for transferring data, e.g. measurement values, from a medical test meter to an optical reading device.

FIG. 8 shows an exemplary control flow for transferring measurement values from a medical test meter 1 to an optical reading device 2. In a first control step S1, the patient takes a measurement with the medical test meter 1. In a further control step S2 the value of the measurement is processed and optionally stored on the meter storage unit 1.3. The control step S2 may comprise detection algorithms to identify the frequency of usage and/or patterns or trends in the measurement values. In a further control step S3 the value of the measurement is presented as a short textual or iconic representation on the meter display 1.2. In the control step S3 the patient is informed whether measurement values are available for transfer to the optical reading device. The patient may ignore these new measurement values. Then the control flow stops along the decision path N. Alternatively the patient may prompt the generation of an optical machine-readable signal 4 along the decision path Y. In a further control step S4 the optical machine-readable signal 4 is generated and displayed on the meter display 1.2.

In a further control step S5 performed on the optical reading device 2, the patient optically connects the optical reading device 2 with the medical test meter 1 such that the optical machine-readable signal 4 is received by the optical receiver 2.6. In a further control step S6 said optical machine-readable signal 4 is decoded. In yet a further control step S7 an explanatory message is generated and displayed on the information display 2.2.1. The explanatory message can be chosen from a list of explanatory messages according to the decoded optical machine-readable signal 4 or retrieved from an external database. The explanatory message may comprise decision trees that can help the patient with deciding what a proper response to the measured value and/or to the detected trend or pattern is. Optionally, in the control step S7 the measurement value and/or the explanatory message and/or information derived thereof is transferred to other embodiments than the information display 2.2.1 of the device output unit 2.2, such as a USB adapter 2.2.2 and/or a GSM adapter 2.2.3. As an example, a medical team treating the patient can be informed about his status. Thus a quick and efficient response to an event or a condition that compromises the therapy of the patient is eased.

It is to be noted that the control steps S1, S2, S3 and S4 are performed on the medical test meter 1, whereas the control steps S5, S6 and S7 are performed on the optical reading device 2.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39), des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A medical device in combination with an optical reading device, the medical device comprising at least one sensor, a meter display for displaying a plurality of independently controllable display elements and a meter controller configured to control the meter display so that a plurality of measurement values measured by the sensor and/or data derived from the sensor are encoded in respective optical machine-readable signals, wherein the optical reading device is adapted to read the optical machine-readable signals from the medical device, to decode the optical machine-readable signals, to interpret a trend or pattern of values measured by the medical device so that a change of medication or of a behavioural pattern of a patient is detected as a potential reason for said trend or pattern, and to generate a message corresponding to the decoded optical machine-readable signals, wherein the message is an explanatory message comprising a recommendation on the behaviour of a patient so as to fulfil at least one predetermined criterion with regard to a value measured by the medical device, and wherein the recommendation comprises a tip to revert said trend or pattern.

2. The medical device in combination with the optical reading device according to claim 1, wherein the plurality of independently controllable display elements comprise independently controllable display elements of a predetermined geometrical form composed in a predetermined geometrical arrangement and wherein the meter controller and/or the meter display are adapted to form the respective optical machine-readable signals as a subset of independently controllable display elements that are switched on.

3. The medical device in combination with the optical reading device according to claim 1, wherein the independently controllable display elements are formed as pixels and wherein the meter controller and/or the meter display are adapted to form each of the respective optical machine-readable signals as a barcode.

4. The medical device in combination with the optical reading device according to claim 1, wherein the independently controllable display elements are formed as pixels, and wherein the meter controller and/or the meter display are adapted to form each of the respective optical machine-readable signals as a two-dimensional code.

5. The medical device in combination with the optical reading device according to claim 4, wherein the two-dimensional code is formed as a DataMatrix Code.

6. The medical device in combination with the optical reading device according to claim 4, wherein the two-dimensional code is formed as a QR Code.

7. The medical device in combination with the optical reading device according to claim 1, wherein at least one of the plurality of independently controllable display elements is varied in its brightness and/or colour over time.

8. The medical device in combination with the optical reading device according to claim 1, wherein the independently controllable display elements are formed as pixels, and wherein the meter controller and/or the meter display are adapted to form each of the respective optical machine-readable signals as a variation of a brightness and/or colour of at least one segment of adjacent pixels over time.

9. The medical device in combination with the optical reading device according to 1, wherein the sensor is formed as a sensor for measuring a blood analyte, in particular blood glucose.

10. The medical device in combination with the optical reading device according to claim 1 further comprising data storage configured to store at least one measurement value and/or value derived from the at least one measurement value, wherein a plurality of measurement values and/or values derived from the at least one measurement value is encoded in the respective optical machine-readable signal.

11. A medical device in combination with an optical reading device, the medical device comprising a meter display for displaying a plurality of independently controllable display elements and the optical reading device comprising an optical receiver with at least one photo-sensitive element, a device storage unit, a device controller and a device output unit, wherein an optical machine-readable signal received with the optical receiver is decoded by the device controller, wherein a message corresponding to the decoded optical machine-readable signal is generated by the device controller and issued by the device output unit, wherein the device controller generates an explanatory message by processing a received decoded optical machine-readable signal, wherein the explanatory message comprises a recommendation on the behaviour of a patient so as to fulfil at least one predetermined criterion with regard to a value measured by the medical device,
wherein the medical device is formed as a drug delivery device,
wherein at least one of the plurality of independently controllable display elements of the meter display of the medical device is varied in its colour over time, and
wherein the optical machine-readable signal received with the optical receiver and decoded by the device controller includes information encoded by a variation of a colour of at least a portion of the optical machine-readable signal over time.

12. The medical device in combination with the optical reading device according to claim 11, wherein the optical receiver comprises a camera.

13. The medical device in combination with the optical reading device according to claim 11, wherein the device output unit is formed as an information display.

14. The medical device in combination with the optical reading device according to claim 11, wherein the device controller generates the explanatory message by processing a stored decoded optical machine-readable signal.

15. The medical device in combination with the optical reading device according to claim 11, wherein the device controller comprises an inference engine for generating the explanatory message.

16. The medical device in combination with the optical reading device according to claim 11, wherein the optical reading device is formed as a mobile phone or personal digital assistant (PDA) comprising a camera, a processing unit, a storage unit, a display and/or a speaker.

* * * * *